United States Patent
Takahashi et al.

(10) Patent No.: US 7,063,721 B2
(45) Date of Patent: Jun. 20, 2006

(54) WOVEN TUBING FOR STENT TYPE BLOOD VASCULAR PROSTHESIS AND STENT TYPE BLOOD VASCULAR PROSTHESIS USING THE TUBING

(75) Inventors: Yoshikazu Takahashi, Kanagawa (JP); Teruhisa Yamazaki, Fukui (JP); Sobei Wakabayashi, Fukui (JP)

(73) Assignees: Terumo Kabushiki Kaisha, Tokyo (JP); Seiren Co., Ltd., Fukui (JP)

( * ) Notice: Subject to any disclaimer, the term of this patent is extended or adjusted under 35 U.S.C. 154(b) by 123 days.

(21) Appl. No.: 10/389,748

(22) Filed: Mar. 18, 2003

(65) Prior Publication Data

US 2003/0181970 A1    Sep. 25, 2003

(30) Foreign Application Priority Data

Mar. 20, 2002  (JP) .............................. 2002-078626

(51) Int. Cl.
    *A61F 2/06*    (2006.01)
(52) U.S. Cl. ..................................... 623/1.51
(58) Field of Classification Search ...... 623/1.49–1.54; 435/29; 264/103; 66/169
    See application file for complete search history.

(56) References Cited

U.S. PATENT DOCUMENTS

| | | | |
|---|---|---|---|
| 4,517,687 A * | 5/1985 | Liebig et al. ............... | 623/1.52 |
| 4,530,113 A * | 7/1985 | Matterson .................. | 623/1.51 |
| 4,718,907 A | 1/1988 | Karwoski et al. | |
| 5,001,331 A * | 3/1991 | Leestemaker ............... | 235/375 |
| 5,017,423 A * | 5/1991 | Bossmann et al. .......... | 442/327 |
| 5,178,630 A * | 1/1993 | Schmitt .................... | 623/1.52 |
| 5,282,848 A * | 2/1994 | Schmitt .................... | 623/1.52 |
| 5,628,788 A * | 5/1997 | Pinchuk .................... | 623/1.2 |
| 5,732,572 A * | 3/1998 | Litton ........................ | 66/195 |
| 5,976,179 A | 11/1999 | Inoue | |
| 6,192,944 B1 * | 2/2001 | Greenhalgh ............. | 139/425 R |
| 6,287,335 B1 | 9/2001 | Drasler et al. | |
| 2003/0204235 A1 * | 10/2003 | Edens et al. .................. | 623/1.5 |
| 2004/0152149 A1 * | 8/2004 | Reid et al. .................... | 435/29 |

FOREIGN PATENT DOCUMENTS

EP          0 464 755 B1    1/1992

\* cited by examiner

Primary Examiner—Suzette J-J Gherbi
(74) Attorney, Agent, or Firm—Buchanan Ingersoll PC (57) ABSTRACT

A woven tubing for use in a stent type blood vascular prosthesis which contains a multifilament formed of two–five single filaments in at least part of warps and has the single filaments disposed in single lines, and a stent type blood vascular prosthesis using the woven tubing are described. The prosthesis combines a shape retaining property that is capable of maintaining its tubular shape without being crushed by the flow of blood with a high liquid tightness that is capable of reducing the leakage of blood to the exterior when implanted at the site of a lesion and allows prevention of the inflow of blood into the site of a lesion.

19 Claims, 6 Drawing Sheets

WOVEN TUBING FOR STENT TYPE BLOOD VASCULAR PROSTHESIS AND STENT TYPE BLOOD VASCULAR PROSTHESIS USING THE TUBING

BACKGROUND OF THE INVENTION

1. Field of the Invention

This invention relates to a woven tubing for a stent type blood vascular prosthesis and to a stent type blood vascular prosthesis using the woven tubing.

2. Description of Related Art

As a means for the remedy of an aortic aneurysm or an aortic dissection, a method which comprises surgically cutting a lesion in the blood vessel and filling the remaining dent therein with a blood vascular prosthesis has been heretofore regarded as a standard. The surgical operation with ventrotomy or thoracotomy inflicts a large burden of invasion on the patient and entrains danger. In particular on the part of old people who suffer from chronic diseases, the application of this surgical operation has been restricted because of inducing a complication. In recent years, as the cure of aortic aneurysm or aortic dissection with low invasion, an intravascular therapy or surgery has been attracting attention. With the intravascular therapy, it is possible to prevent the inflow of blood to the lesion and protect the lesion against fracture by guiding a blood vascular prosthesis endowed with a stent, namely a stent type blood vascular prosthesis, into the lesion in the blood vessel via a catheter and covering the lesion with the tenting blood vascular prosthesis thereby thrombogenesing the lesion.

The stent type blood vascular prosthesis, which is used for this intravascular therapy, is inserted as folded in a small size into the catheter, conveyed to the lesion, and then allowed to unfold and restore the original tubular shape. The term "stent" as used herein refers to a tubular supporting skeleton, which is inserted into an intracorporeal tubular organ such as the blood vessel for supporting the organ. In the blood vascular prosthesis, the stent functions to hold the blood vessel in its tubular shape mechanically and implant the blood vascular prosthesis fast against the wall of the blood vessel. However, the stent type blood vascular prosthesis has limited folding ability and insufficient adaptability to curved blood vessels in human bodies because it is inferior in flexibility to the blood vascular prosthesis that is devoid of stent.

U.S. Pat. No. 5,976,179 discloses an implanting device (equivalent to the "stent type blood vascular prosthesis" designated in the present specification) which has a plurality of intermittently disposed bendable wire rings (equivalent to the "stent" designated in the present specification) concatenated with the tubular surface member (equivalent to the "woven tubing" designated in the present specification). Unlike the conventional stent, which is provided with supporting skeletons concatenated continuously in the direction of length, in the stent disclosed in the publication individual wire rings for constructing such a stent are not concatenated. This stent relies on this construction to attain an implanting device which prevents degradation of flexibility and excels in folding ability and adaptability to curved blood vessels in human bodies. Further, by using a monofilament having a shape retaining property as warps and a dense multifilament as wefts in the surface member, the surface member is aimed at attaining such a shape retaining property as avoids being crushed by the flow of blood and such a liquid tightness (low water permeability) as avoids leakage of blood to the exterior in the implanting devices even when the wire rings are not concatenated.

SUMMARY OF THE INVENTION

The implanting device mentioned above is characterized by the combination of the wire rings and the surface member. That is to say, the wire rings themselves have no ability whatever to resist the crush exerted in the direction of the length of the device. When the wire rings are combined with the conventional surface member which pays no consideration to the crush, therefore, this combination could possibly constitute a fatal defect because the flow of blood crushes the implanting device and the blood flows through the gap in the terminal part into the lesion.

The use of a monofilament as warps, however, has brought another problem that readily gives wale streaks on the coats of the surface member. The wale streaks are faults which arise in the process of weaving owing to the lack of adequacy in the tension of warps, the number of the drawing-in thread through reeds, and the number of dent per unit length. They occur when scratches on warps and gaps between adjacent warps happen to manifest themselves as streaks. They are unfavorable because they lower strengths such as tensile strength, bursting strength, and liquid tightness. Further, the use of a monofilament as warps brings yet another problem that readily induces occurrence of gaps at interlacing parts of warps and wefts. The gaps cause a serious degradation of liquid tightness. The surface member which uses a monofilament as warps offers no sufficient liquid tightness even if a dense multifilament is adopted as wefts, and fail to prevent the inflow of blood into the lesion owing to leakage of blood.

The gaps between the warps and the wefts are eliminated by using a multifilament as warps. However, the surface member, which uses the conventional multifilament as warps, offers no sufficient durability to withstand the crush inflicted in the direction of length and, therefore, cannot be combined with a stent having no durability to withstand the crush such as a stent which acquires enhanced flexibility by having wire rings disposed intermittently. Meanwhile, when the surface member which uses the conventional multifilament as the warps is combined with a stent having durability to withstand the crush, such as a stent that has supporting skeletons concatenated in the direction of length in the Z-stent made of stainless steel, it is compelled to sacrifice flexibility. Thus, no stent type blood vascular prostheses satisfying flexibility, shape retaining property, and liquid tightness wholly exist. This situation has hindered the cure of aortic aneurysm or aortic dissection.

This invention has been produced in view of such true state of prior art.

An object of this invention is to provide a woven tubing for a stent type blood vascular prosthesis (It may be referred to simply as "WTVP".), which combines a shape retaining property that is able to retain the tubular shape thereof without being crushed by the flow of blood with a high liquid tightness enough to reduce the leakage of blood to the exterior when a stent type blood vascular prosthesis (It may be simply referred to as "SBVP".) including the WTVP is implanted at the site of a lesion and allows prevention of the inflow of blood into the lesion.

Another object of this invention is to provide a SBVP that uses the WTVP mentioned above.

After repeating diligent studies with a view to solving the problems mentioned above, we have found that it is really effective in accomplishing the objects to use a multifilament with a specific number of single filaments as warps of the WTVP and dispose the single filaments in single lines within wefts. This invention has been achieved as a result.

This invention is composed of the following aspects. A WTVP is characterized by containing at least part of multifilament formed of 2–5 single filaments as warps and having the single filaments disposed in single lines within wefts.

A SBVP is characterized by comprising the WTVP and a stent.

In accordance with the WTVP of this invention, by using a multifilament which has the number of the single filament within a specific range and preferably has the number of the single filament, the size of the single filament, the total size, and the twist multiplier in respective specific ranges in at least part of the warps, both a shape retaining property that is able to retain the tubular shape thereof without being crushed by the flow of blood and a high liquid tightness enough to reduce the leakage of blood to the exterior when it is implanted as a SBVP at the site of a lesion are acquired. It is consequently enabled to prevent the inflow of blood into the site of a lesion.

The WTVP of this invention can be advantageously applied even to a stent which, when used by itself, offers no durability to withstand the crush in the direction of length, consequently enabled to give rise to a SBVP which is excellent in flexibility and conformability and really useful in the intravascular therapy.

The WTVP of this invention, owing to the good shape retaining property thereof, can be applied to a stent that is devoid of durability to withstand the crush in the direction of length. When it is combined with a stent that has wire rings disposed intermittently, for example, it can provide a SBVP with flexibility that can be inserted as folded in a small size into the catheter and allowed to conform to the shape of a human blood vessel.

The above and other objects, features and advantages of the present invention will become clear from the following description of the preferred embodiments.

BRIEF DESCRIPTION OF DRAWINGS

The accompanying drawing incorporated in and forming a part of the specification, illustrates several aspects of the present invention, and together with the description serve to explain the principles of the invention. In the drawings.

DESCRIPTION OF THE PREFERRED EMBODIMENTS

Now, this invention will be described below with reference to embodiments. The term "woven tubing" refers to a tube obtained by joining the opposite edges of a flat woven fabric by sewing or fusion, or a tube formed from the stage of weaving by the technique of hollow weave, namely by having a weft woven spirally in the circumferential direction between warps disposed along the direction of length.

Figure 4:
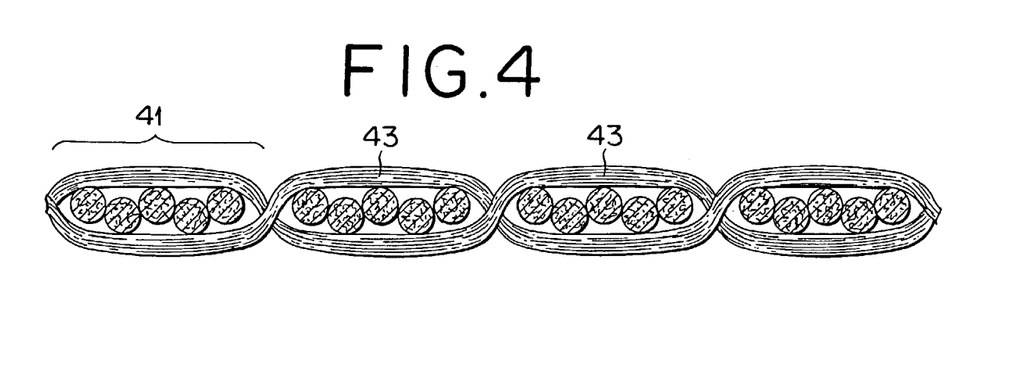
FIG. 4 is a cross section illustrating the allowed arrangement of single filaments of warps within wefts in a WTVP.
Figure 5:
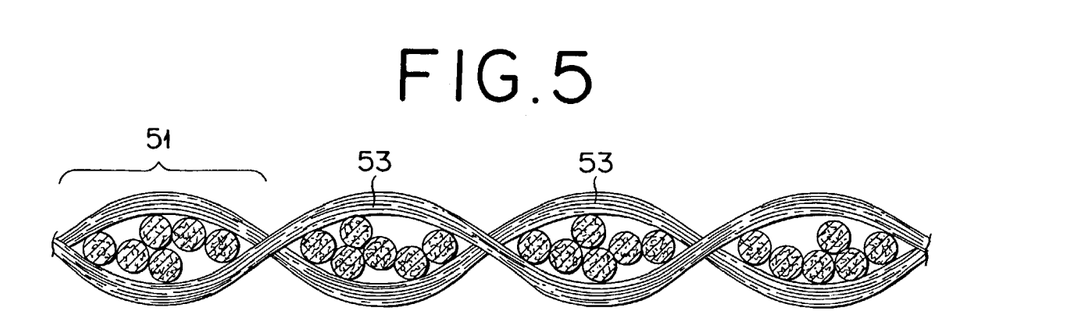
FIG. 5 is a cross section illustrating the arrangement of single filaments of warps within wefts in a WTVP obtained in Comparative Example 3.

The WTVP of this invention contains, in at least part of warps, a multifilament formed of 2–5 single filaments in which such single filaments are disposed in single lines between the wefts. These multifilaments, as will be illustrated in FIGS. 1–3 below, are disposed in such a state that single filaments, 11$a$, 11$b$; 21$a$, 21$b$, 21$c$; and 31$a$, 31$b$, 31$c$, 31$d$, 31$e$, which form warps 11, 21, and 31, respectively, may be arranged in single lines respectively within wefts 13, 23, and 33. Naturally, the vertical reversal of this arrangement is also embraced by this description. By having a specific number of single filaments disposed in single lines as described above, it is possible to reduce gaps between warps and wefts and to reduce coefficient of water permeability of the WTVP to a relatively low level or to attain a high liquid tightness while increasing column strength thereof or maintaining a shape retaining property. The expression "in single lines" means that the single filaments are arranged substantially in a single line. Specifically, this expression is so extensive as to allow application up to the state of wefts 43 and warps 41 illustrated in FIG. 4, but excludes the states illustrated in FIGS. 5 and 6. As shown in FIG. 5, when the respective single filaments 51 as the warp are a state of overlapping, the distance between wefts 53 is enlarged and coefficient of water permeability thereof cannot be maintained or a high liquid tightness thereof cannot be attained. This is also applied to FIG. 6, in which 61 depicts the respective single filaments and 63 the wefts. In the present invention, the envelope of the warp by the function of the weft is preferred to assume an elliptical or depressed shape.

Figure 7:
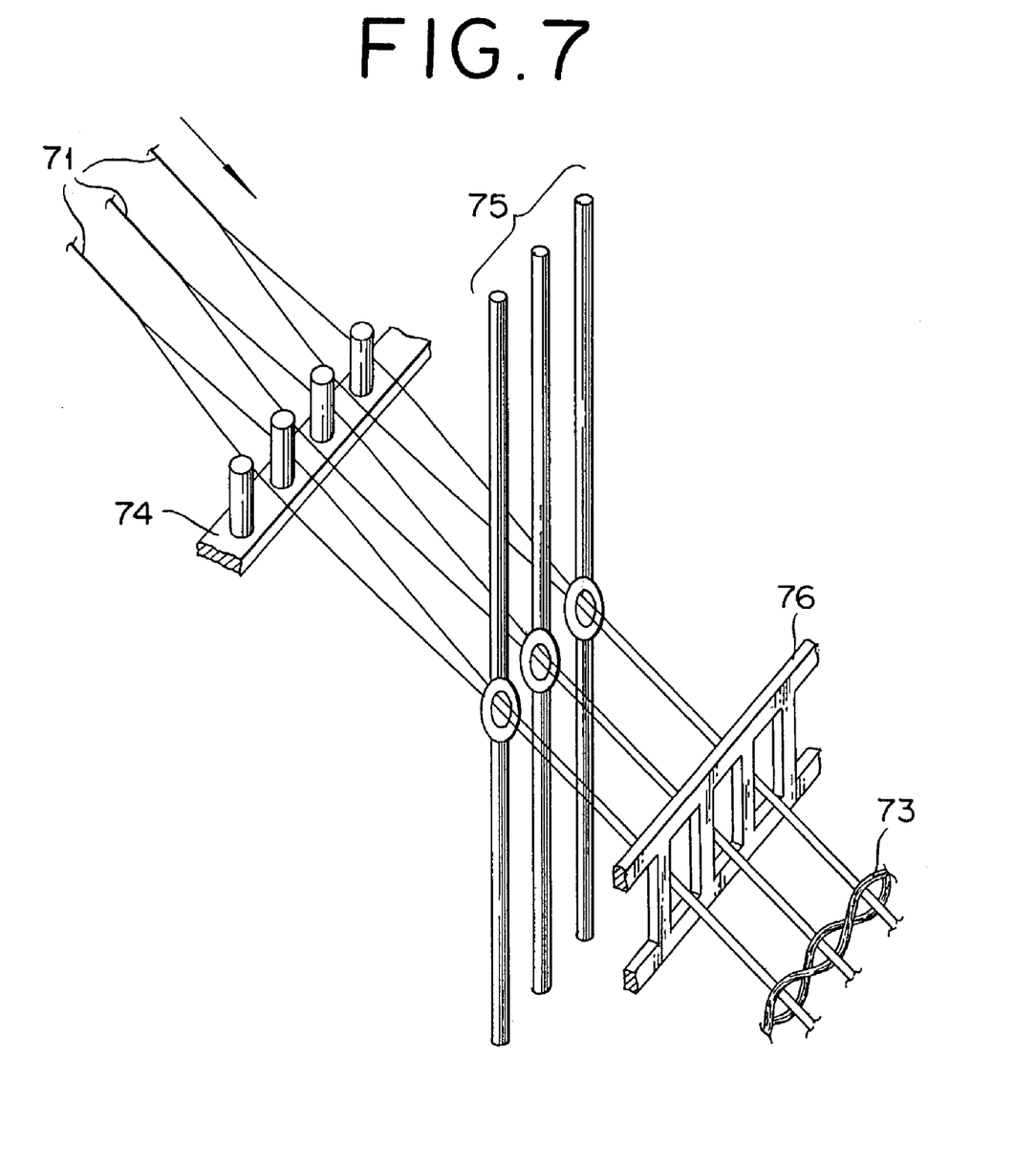
FIG. 7 is a schematic diagram of a device for forming the state of disposition in single lines.

FIG. 7 is a schematic diagram of a device for forming a state of disposal in single lines. In order to form the state of disposal in single lines, it can be cited, as shown for example in FIG. 7, a manner comprising dividing warps 71, multifilaments consist of two single filaments, with a separator 74, a heald 75 and a reed 76 into individual single filaments, aligning the divided filaments, and supplying them to a weaving part to be interlaced with weft 73 therein.

The multifilament which is used in the warps of this invention is not particularly restricted but only required to be formed of 2–5 single filaments. It preferably has the following characteristics (a)–(c).

(a) The size of the single filament is in the range of 5.5–50 dtex. If the size is smaller than 5.5 dtex, the single filament itself and the multifilament formed thereof will be deficient in stiffness. The woven tubing using the multifilament in at least part of the warps and a SBVP using the WTVP fail to acquire a sufficient shape retaining property and fail to offer sufficient durability to withstand the crush inflicted in the direction of length. If the size exceeds 50 dtex, the WTVP and a SBVP using the WTVP will not be easily folded into a small size because of an increased wall thickness and unduly large stiffness of the WTVP. As a result, the catheter used in the intravascular therapy will be required to have such a large diameter that it may not be inserted easily into or moved in the blood vessel and may even have the possibility of damaging the site of a lesion.

If the number of the single filament is one, i.e., a monofilament, the WTVP will tend to give rise to wale streaks or gaps between warps and wefts, betray deficiency in strength such as tensile strength, bursting strength, and liquid tightness, and fail to prevent leakage of blood. If the number exceeds 5, the WTVP will possibly be deficient in liquid tightness because the single filament readily twists around or overlap one another and the single filaments are not easily disposed in single lines within wefts.

(b) The total size of the multifilament, which is formed as described above, is in the range of 11–250 dtex. If the total size is smaller than 11 dtex, the stiffness will be small. As a result, the WTVP using the multifilament in at least part of the warps and a SBVP using the WTVP will fail to acquire a sufficient shape retaining property and will fail to offer sufficient durability to withstand the crush in the direction of length. If the total size exceeds 250 dtex, the WTVP and the SBVP will not be easily folded into a small size because of an increased wall thickness and unduly large stiffness thereof. As a result, the catheter used in the intravascular therapy will be required to have such a large diameter that it may not be inserted easily into or moved in the blood vessel and may even have the possibility of damaging the site of a lesion. More preferably, the multifilament has a total size in the range of 30–80 dtex and can be obtained by properly adjusting the size of the single filament, 5.5–50 dtex, and the number of the single filament, 2–5, in the respective ranges mentioned above.

The individual single filament, which form the multifilament, may be that having the same size or that having severally different sizes so long as the multifilament satisfies the conditions mentioned above.

(c) Twist multiplier of the multifilament is in the range of 0–100 times/meter. Since the multifilament which are formed of 2–5 single filaments having a size in the range of 5.5–50 dtex are large in size of the single filament and small in number of the single filament as compared with the conventional multifilament used as the raw material for the blood vascular prosthesis, namely formed of 10–1000 single filaments having a size in the range of 0.1–3.5 dtex, the mutual entangling and the overlapping of single filaments which are induced by the impartation of twists will largely affect the liquid tightness. The twist multiplier, therefore, is preferred to be 0 time/meter (absence of twist) or to be infinitely close to 0 time/meter and is not tolerated to exceed 100 times/meter at most. When the twist multiplier is not more than 100 times/meter, the twists are undone during the course of weaving and the resultant single filaments are disposed in single lines within wefts. If the twist multiplier exceeds 100 times/meter, the woven tubing will suffer from deficiency in liquid tightness and fail to prevent the leakage of blood because the twists are not perfectly undone during the course of weaving and the resultant single filaments are not disposed in single lines within the wefts.

The WTVP of this invention uses, in at least part of warps forming the woven tubing, a multifilament which has the number of the single filament within a specific range and preferably has the number of the single filament, the size of the single filament, the total size, and the twist multiplier in respective specific ranges (which may be referred to as "the present multifilament"), and causes the single filaments to dispose in the state of single lines within the wefts. As a result, the WTVP, when implanted at the site of a lesion as a SBVP, combines a shape retaining property which suffices to retain the tubular shape thereof without being crushed by the flow of blood with a high liquid tightness enough to reduce the leakage of blood to the exterior, and allows prevention of the inflow of blood into the lesion. The WTVP of the present invention is characterized by disposing the single filaments of the warp, which uses a specific multifilament, in the single line within the weft. Otherwise, when 2–5 monofilaments that are caused to parallel and disposed in a state of the single line, are used instead of the present multifilament, the monofilaments will also produce the advantage effects of the present invention. The size of the monofilament to be used in the present invention is preferred to be in the range of 5.5–50 dtex.

The threads or strands other than the multifilament that is used in the warps (which may be occasionally referred to as "other threads") are not particularly restricted. For example, the multifilament heretofore used as the raw material for the blood vascular prosthesis, namely formed of 10–1000 single filaments having a single filament size in the range of 0.1–3.5 dtex, may be used as "other threads."

If the size of the single filament is smaller than 0.1 dtex, the WTVP will be deficient in strengths such as tensile strength and bursting strength. If the size of the single filament exceeds 3.5 dtex, the single filament, when used in combination with the present multifilament, will render the WTVP and a SBVP using the WTVP difficult to be folded in a small size because of an increased wall thickness and an increased stiffness.

If the number of the single filament is smaller than 10, the WTVP will betray deficiency in liquid tightness and fail to prevent the leakage of blood. If the number exceeds 1000, the filament will tend to incur troubles such as warp breakages and fluff during the course of weaving and impair the operational stability.

The multifilament constructed as described above are preferred to have a total size in the range of 33–110 dtex. If the total size is smaller than 33 dtex, the WTVP, combined with the present multifilament, will betray deficiency in strengths such as tensile strength and bursting strength. If the total size is larger than 110 dtex, the WTVP and a SBVP using the WTVP will not be easily folded in a small size because of an increased wall thickness and an undue addition to stiffness.

The other threads to be used in the warps may be properly selected from the multifilament mentioned above, preferably a multifilament which has a similar total size to the present multifilament to be combined. If the multifilament to be used in the warps is notably different in total size from the other threads in the warps, the WTVP will form a nonuniform surface and possibly betray deficiency in liquid tightness. It will further entail wide dispersion of strengths such as tensile strength and bursting strength and of wall thickness as well.

The twist multiplier of the multifilament is preferred to be in the range of 0–1000 times/meter. The smaller the twist multiplier, the less the mutual entangling and the overlapping of the single filaments occur. Thus, the liquid tightness is enhanced. The twist multiplier of not more than 1000 times/meter is allowable from the viewpoint of the stability of weaving. If the twist multiplier exceeds 1000 times/meter, the mutual entangling and the overlapping thereof will have adverse influences and then the woven tubing will have insufficient liquid tightness. The twist multiplier of the multifilament is preferred to be in the range of 200–500 times/meter for the sake of the balance between the stability of weaving and the liquid tightness.

The ratio of the present multifilament to the other threads in the warps is preferred to be in the range of 25:75–100:0 on the assumption that the total number of warps forming the woven tubing is 100. The other threads and the multifilament are preferred to be disposed uniformly. If the ratio is smaller than 25:75, the WTVP and a SBVP using the WTVP will not acquire a sufficient shape retaining property and will offer no sufficient durability to withstand the crush in the direction of length. By adjusting the ratio in the range of 25:75–100:0, it is possible to adjust such a durability. That is to say, the durability of the WTVP and SBVP increases in accordance as the ratio the multifilament is increased.

The wefts for forming the WTVP are not particularly restricted. Similarly to the other threads to be used in the warps, the following multifilament may be used as the wefts: a multifilament which has been heretofore used as the raw material for the blood vascular prosthesis, i.e. a multifilament having a single filament size in the range of 0.1–3.5 dtex, preferably 0.1–1.0 dtex, and formed of 10–1000 single filaments. If the size of the single filament is in the range of 0.1–1.0 dtex, the WTVP will gain further in denseness and enjoy enhanced liquid tightness. The multifilament having a total size in the range of 33–110 dtex and a twist multiplier in the range of 0–1000times/meter, preferably 200–500 times/meter prove particularly advantageous.

By using the multifilament satisfying the conditions mentioned above in the wefts of the WTVP, it is possible to make the most of the liquid tightness, which is one of the merits of this invention, without impairing strengths such a stensile strength and bursting strength and folding ability.

Though the raw material for the present multifilament to be used in the warps, other threads to be used in the warps and threads to be used in the wefts is not particularly restricted, it is preferred to be polyester type fibers from the actual results of use as the material for a blood vascular prosthesis. The polyester type fibers have been widely used as the raw material for blood vascular prosthesis because they have chemical stability, great durability, and high mechanical strength and avoid exhibiting toxicity or producing any foreign body reaction. As examples of polyester type fibers, polyethylene terephthalate, polybutylene terephthalate, polyester-polyether block copolymers, and composite fibers thereof may be cited.

The textile design of the WTVP is not particularly restricted but includes, for example, plain weave, twill weave, satin weave, or crepe weave. Among other weaves, the plain weave proves particularly favorable because it permits easy formation of a tubular article having a small wall thickness and excelling in strengths such as tensile strength and bursting strength and in liquid tightness.

The WTVP of this invention, which is obtained as described above, combines a shape retaining property that is able to retain the tubular shape thereof without being crushed by the flow of blood with a high liquid tightness enough to reduce the leakage of blood to the exterior when the WTVP is implanted as a SBVP at the site of a lesion. In particular, the WTVP which has the magnitudes of column strength, radius of kink, coefficient of water permeability, and wall thickness within respectively specified ranges, excels not only in the shape retaining property and the liquid tightness which are the salient merits of this invention but also in the kink resistance and the folding ability which ought to be naturally endowed for the SBVP. Thus, it is quite useful for the intravascular therapy.

The column strength of the WTVP is preferred to be in the range of 0.020–0.130 N/mm of diameter. The term "column strength" as used herein represents the strength or durability to withstand the crush in the direction of length. The larger the value of the column strength is, the higher the durability to withstand the crush in the direction of length is. If the column strength is smaller than 0.020 N/mm of diameter, the WTVP, when implanted at the site of a lesion as a SBVP, will possibly be crushed by the flow of blood and compelled to yield to the inflow of blood into the site of the lesion. If the column strength exceeds 0.130 N/mm of diameter, folding the WTVP and SBVP into a small size will become difficult because of an increased stiffness. The WTVP or SBVP further will not easily follow the blood vessel after the WTVP or SBVP has been implanted therein.

The radius of a kink in the WTVP varies with the inside diameter thereof and tends to increase in proportion to the size of inside diameters. Though the radius of a kink, therefore, cannot be uniquely defined, it is preferred to be not more than 5.5 mm when the WTVP has an inside diameter of 24 mm, for example. The term "kink" as used herein refers to the phenomenon in which the blood vascular prosthesis is folded under the inner flexure of a body or the external pressure. The kink resistance is expressed by the radius of a kink, namely such a radius of the loop formed in a given blood vascular prosthesis as forms a clearly discernible bend therein. The smaller the value of the radius of a kink is, the larger the durability to withstand the bend is. The radius of a kink is preferred to be as near to 0 mm as possible for the sake of facilitating the insertion and implant of a SBVP using the WTVP even to a complicated bent portion in the blood vessel. The radius of a kink in the WTVP of this invention is preferred to be not more than 5.5mm when the inside diameter of the WTVP is assumed to be 24 mm. If the radius is larger than 5.5 mm, a SBVP will fail to conform to a flexural curved human blood vessel when the WTVP is implanted as the SBVP at the site of a lesion.

The WTVP of this invention is primarily supposed to be applied to the therapy of an aortic aneurysm or an aortic dissection in combination with a stent. The inside diameter of this WTVP may be in the range of 7–54 mm. On account of the possibility of personal equation, however, it is not limited to this range.

The WTVP is preferred to have undergone a crimp treatment. The application of this crimp treatment improves the WTVP and a SBVP using the WTVP of this invention in the ability of flexion to the extent of enabling them to conform naturally to the shape of a human blood vessel. In other words, the radius of a kink is decreased and the kink resistance is enhanced. Further, the crimps consequently imparted to the WTVP produce an effective action in the restoration of the SBVP using the WTVP from the folded state to the original shape. The method for imparting such crimps to the WTVP may be selected from among the known methods such as those described in U.S. Pat. No. 3,337,673 and JP-A-1-155860.

The coefficient of water permeability of the WTVP is preferred to be not more than 500 mL/min/cm$^2$. The coefficient of water permeability is closely related to the liquid tightness. More preferably, this magnitude is 0 mL/min/cm$^2$ or approximates closely to 0 mL/min/cm$^2$ for the sake of exalting the degree with which the leakage of blood from the WTVP can be prevented and the thrombogenesis can be promoted. The upper limit of the preferred coefficient of water permeability is 500 mL/min/cm². If the coefficient is larger than this upper limit, the WTVP, when implanted in the site of a lesion as a SBVP, will possibly suffer blood to leak therefrom and fail to prevent the inflow of blood into the site of the lesion.

The wall thickness of the WTVP is preferred to be not more than 150 µm. If the wall thickness is larger than 150 µm, the WTVP and a SBVP using the WTVP will not be easily folded into a small size. The folding ability, as previously mentioned, is an important parameter in the construction of the SBVP. If the SBVP is deficient in folding ability, it will require the catheter used in the intravascular therapy to have a large diameter and will lower operational efficiency.

The WTVP may be furnished with a branching part. When an aneurysm is formed in a branching part of a vital blood vessel, e.g., from the abdominal aorta to the common iliac artery, it is conceivable to perform the therapy by using a plurality of straight SBVPs, though the relevant surgical operation is complicated and consumes an unduly long time. In this case, the use of a SBVP furnished with a branching part is advantageous and rational from the viewpoint of lightening the burden on the patient and ensuring the safety of the operation.

The WTVP of this invention is preferred to be applied to the stent disclosed in U.S. Pat. No. 5,976,179, namely the stent which, as represented by a stent having wire rings disposed intermittently and made of titanium-nickel alloy et al, is not possessed in itself of the durability to withstand the crush in the direction of length. Further, the WTVP of this invention can manifest more effectively the merit of this invention which resides in excelling in the shape retaining property, though it is not restricted by this manifestation.

Further, owing to the merit of excelling in the shape retaining property and the liquid tightness, the WTVP can be effectively used as a blood vascular prosthesis that is devoid of a stent.

Figure 8:
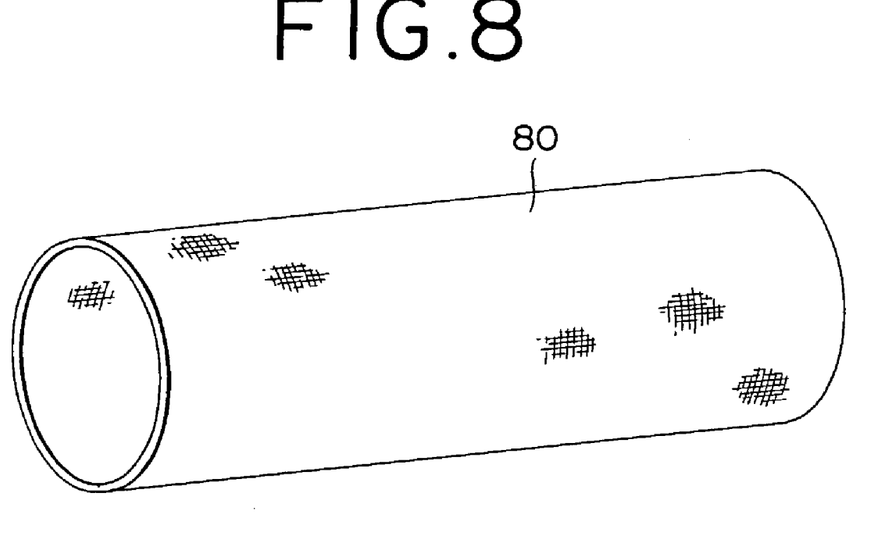
FIG. 8 is a schematic diagram showing a WTVP.

FIG. 8 is a schematic diagram showing a WTVP. In FIG. 8, 80 is a WTVP.

Figure 9:
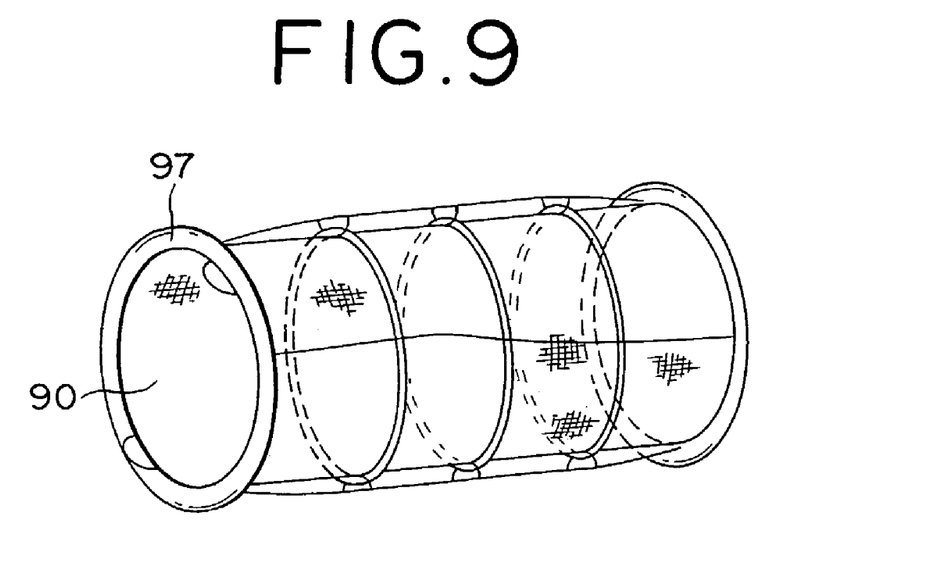
FIG. 9 is a schematic diagram showing a SBVP in which a WTVP is inner attached to the SBVP.

FIG. 9 is a schematic diagram showing a SBVP. In FIG. 9, a WTVP 90 is innerly attached to a stent 97.

EXAMPLES

Now, this invention will be described more specifically below with reference to examples. It should be noted, however, that this invention is not limited to the examples.

Methods of Determination

Column Strength (N/mm in diameter)

The force required for crushing a sample of woven tubing 50 mm in length to a length of 30 mm is measured with a tensile or compression test machine. The denomination "mm in diameter" denotes the magnitude of the inside diameter of a given WTVP.

Radius of a Kink (mm)

The measurement of this magnitude is performed by consulting ISO7198 Cardiovascular implants-Tubular vascular prostheses. Such a radius of the loop formed in a given woven tubing as formed a clearly discernible fold is measured with a cylindrical jig of a known radius. The retention of the inner pressure of the sample tubing is omitted for rating the characteristics of the woven tubing itself.

Coefficient of Water Permeability (mL/min/cm²)

The measurement of this magnitude is performed by consulting ISO7198 Cardiovascular implants-Tubular vascular prostheses. This magnitude is measured by supplying water under 120 mmHg (16.0 kPa) to the surface of a sample 0.5–1.0 cm² in area and measuring the quantity of the water which had permeated the sample in one minute. The quantity of permeating water consequently found is reduced to the rate per 1.0 cm² and reported as the coefficient of water permeation. The determination of the coefficient of water absorption is performed on a sample of woven tubing which has not yet undergone the crimp treatment.

Wall Thickness (µm)

The measurement of this magnitude is performed with a constant pressure thickness meter by consulting ISO7198 Cardiovascular implants-Tubular vascular prostheses. This measurement is performed on a sample of woven tubing that has not yet undergone the crimp treatment.

Example 1

Figure 1:
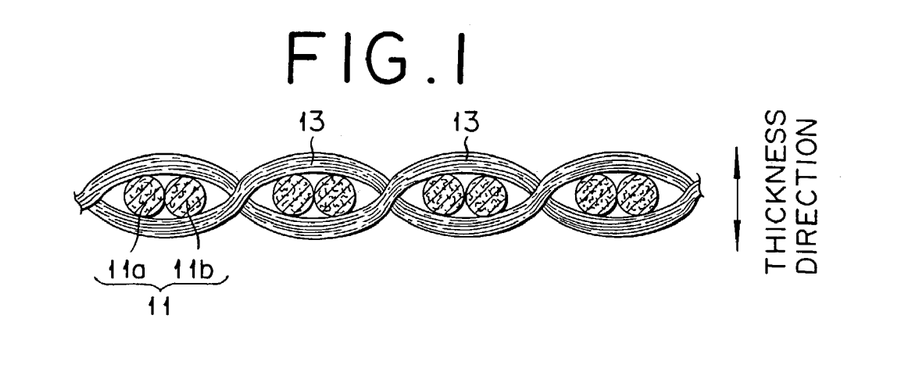
FIG. 1 is a cross section illustrating the arrangement of single filaments of warps within wefts in a WTVP obtained in Example 1.

A tubing of plain weave design 24 mm in inside diameter was formed by hollow weave using an untwisted multifilament of polyethylene terephthalate having a single filament size of 18 dtex and formed of two single filaments to a total size of 36 dtex (the present multifilament) for warps and a multifilament of polyethylene terephthalate having a single filament size of 0.55 dtex and formed of 170 single filaments to a total size of 94 dtex and endowed with a twist multiplier of 200 times/meter for wefts. The tubing was further subjected to a crimp treatment to obtain a target WTVP. The state of warps in the produced WTVP is schematically illustrated in FIG. 1.

Example 2

A target WTVP was obtained by repeating the procedure of Example 1, except that an untwisted multifilament of polyethylene terephthalate having a single filament size of 33.5 dtex and formed of two single filaments to a total size of 67 dtex (the present multifilament) was used for warps. In the WTVP consequently obtained, the single filaments of the warps were disposed in single lines.

Example 3

A target WTVP was obtained by repeating the procedure of Example 1, except that an untwisted multifilament of polyethylene terephthalate having a single filament size of 16.8 dtex and formed of four single filaments to a total size of 67 dtex (the present multifilament) was used for warps. In the WTVP consequently obtained, the single filaments of the warps were disposed in single lines.

Example 4

Figure 2:
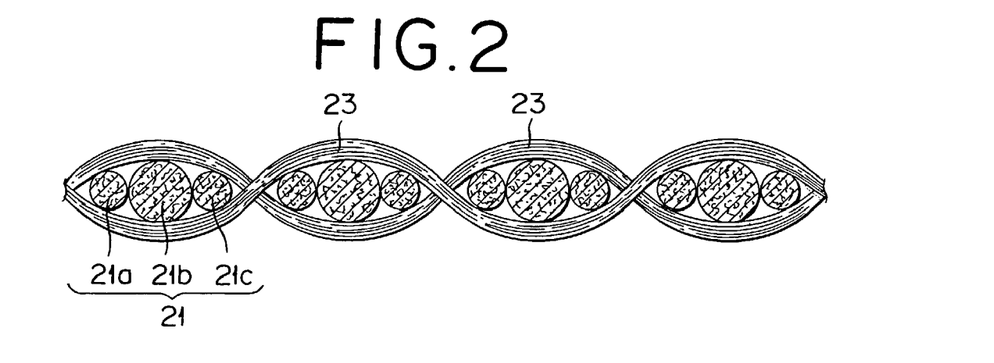
FIG. 2 is a cross section illustrating the arrangement of single filaments of warps within wefts in a WTVP obtained in Example 4.

A target WTVP was obtained by repeating the procedure of Example 1, except that an untwisted multifilament of polyethylene terephthalate formed of one single filament of a single filament size of 33 dtex and two single filaments of a single filament size of 18 dtex to a total size of 69 dtex (the present multifilament) was used for warps. The state of warps in the WTVP consequently obtained is schematically illustrated in FIG. 2.

Example 5

A target WTVP was obtained by repeating the procedure of Example 1, except that an untwisted multifilament of polyethylene terephthalate having a single filament size of 18 dtex and formed of two single filaments to a total size of 36 dtex (the present multifilament) and a multifilament of polyethylene terephthalate having a single filament size of 2.8 dtex, formed of 12 single filaments to a total size of 33 dtex, and endowed with a twist multiplier of 300 times/meter at a ratio of 50:50 were used for warps. In the WTVP consequently obtained, the single filaments of the warps were disposed in single lines.

Example 6

A target WTVP was obtained by repeating the procedure of Example 1, except that an untwisted multifilament of polyethylene terephthalate having a single filament size of 50 dtex and formed of four single filaments to a total size of 200 dtex (the present multifilament) was used for warps. In the WTVP consequently obtained, the single filaments of the warps were disposed in single lines.

Example 7

Figure 3:
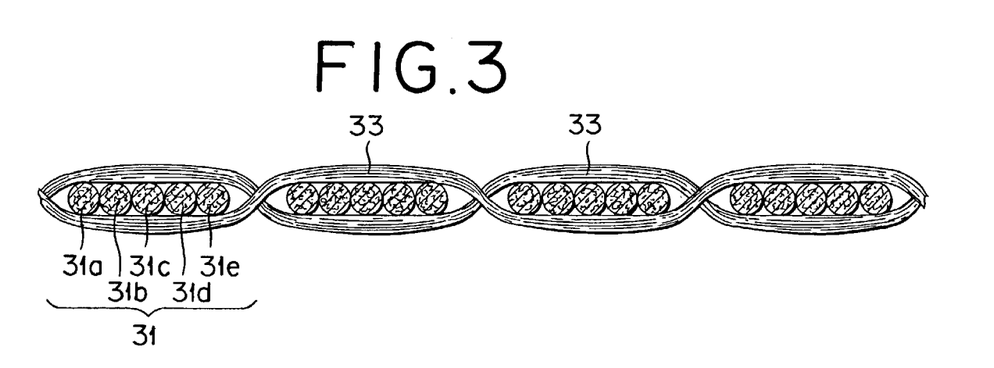
FIG. 3 is a cross section illustrating the arrangement of single filaments of warps within wefts in a WTVP obtained in Example 7.

A target WTVP was obtained by repeating the procedure of Example 1, except that an untwisted multifilament of polyethylene terephthalate having a single filament size of 18 dtex and formed of five single filaments to a total size of 90 dtex (the present multifilament) was used for warps. The state of warps in the WTVP consequently obtained is schematically illustrated in FIG. 3.

Example 8

A target WTVP was obtained by repeating the procedure of Example 1, except that a multifilament of polyethylene terephthalate having a single filament size of 18 dtex and formed of five single filaments to a total size of 90 dtex and endowed with a twist multiplier of 100 times/meter (the present multifilament) was used for warps. In the WTVP consequently obtained, the single filaments of the warps were disposed in single lines.

Comparative Example 1

A WTVP was obtained by repeating the procedure of Example 1, except that a monofilament of polyethylene terephthalate having a size of 18 dtex was used for warps.

Comparative Example 2

A WTVP was obtained by repeating the procedure of Example 1, except that a monofilament of polyethylene terephthalate having a size of 33 dtex was used for warps.

Comparative Example 3

A WTVP was obtained by repeating the procedure of Example 1, except that an untwisted multifilament of polyethylene terephthalate having a single filament size of 18 dtex and formed of six single filaments to a total size of 108 dtex were used for warps. The state of warps in the WTVP consequently obtained is schematically illustrated in FIG. 5.

Comparative Example 4

A WTVP was obtained by repeating the procedure of Example 1, except that a multifilament of polyethylene terephthalate having a single filament size of 2.3 dtex and formed of 24 single filaments to a total size of 56 dtex and endowed with a twist multiplier of 300 times/meter for warps.

Comparative Example 5

A WTVP was obtained by repeating the procedure of Example 1, except that a multifilament of polyethylene terephthalate having a single filament size of 4.6 dtex and formed of 48 single filaments to a total size of 222 dtex and endowed with a twist multiplier of 300 times/meter were used for warps.

Comparative Example 6

Figure 6:
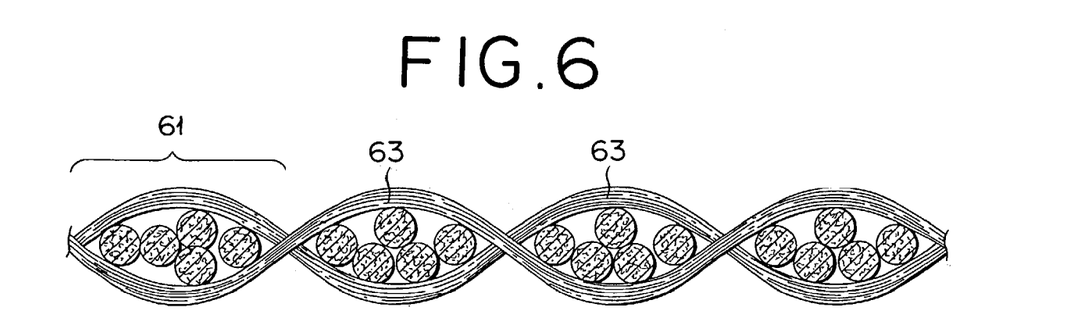
FIG. 6 is a cross section illustrating the arrangement of single filaments of warps within wefts in a WTVP obtained in Comparative Example 6.

A WTVP was obtained by repeating the procedure of Example 1, except that a multifilament of polyethylene terephthalate having a single filament size of 18 dtex and formed of five single filaments to a total size of 90 dtex and endowed with a twist multiplier of 150 times/meter were used for warps. The state of warps in the WTVP consequently obtained is schematically illustrated in FIG. 6.

Comparative Example 7

A commercially available blood vascular prosthesis (made of polyethylene terephthalate, measuring 24 mm in inside diameter, formed by hollow weave in plain weave design, and undergone a crimp treatment) was evaluated with respect to performance.

The size and the number of the single filament used in the prosthesis were found as follows. Cross sections of the filament forming the prosthesis were observed under an electron microscope to find the number and diameters of the single filament. Then, the single filament size was calculated from the diameters of single filaments and the total size was calculated from the single filament size and the number of the single filament. As a result, the warp was found to be multifilaments having a single filament size of 0.58 dtex and formed of 216 single filaments formed to a total size of 125 dtex and the weft was found to be multifilaments having a single filament size of 0.58 dtex and formed of 144 single filaments to a total size of 84 dtex. Incidentally, the coefficient of water permeability and the wall thickness were measured of a blood vascular prosthesis which had been deprived of crimps by a heat treatment.

Figure 10:
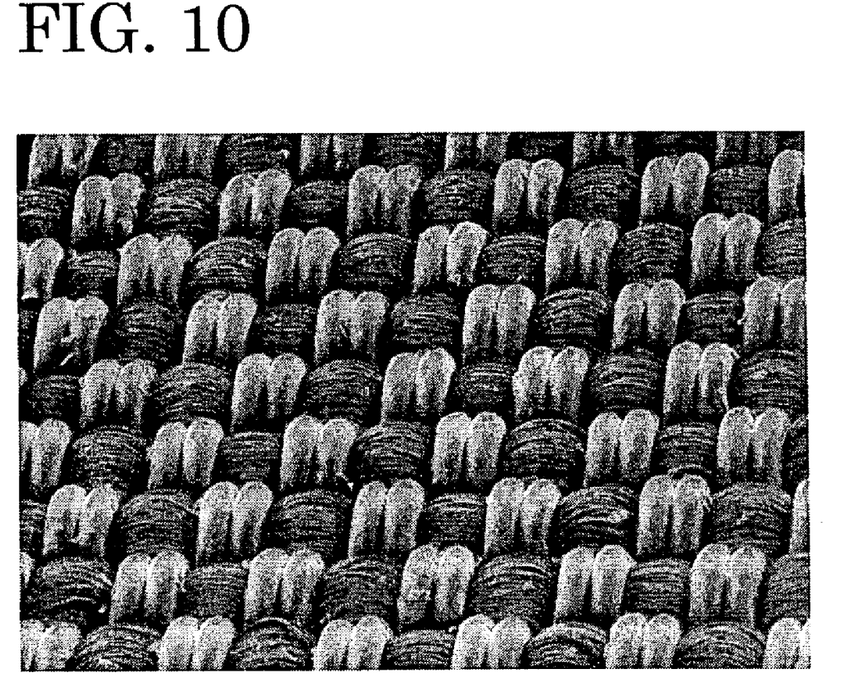
FIG. 10 is a photograph illustrating a magnified surface of the WTVP obtained in Example 1 for use in a SBVP.
Figure 11:
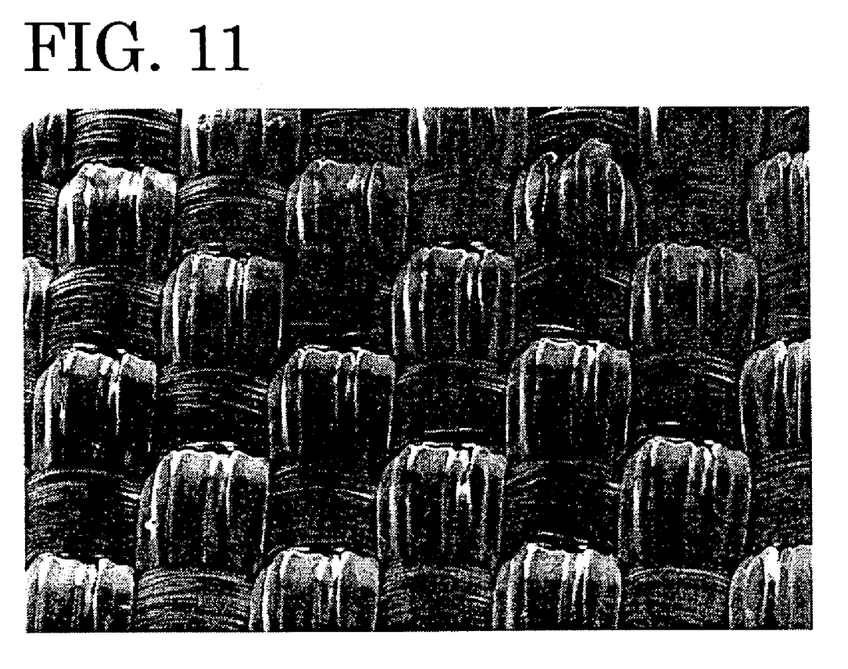
FIG. 11 is a photograph illustrating a magnified surface of the WTVP obtained in Example 3 for use in a SBVP.
Figure 12:
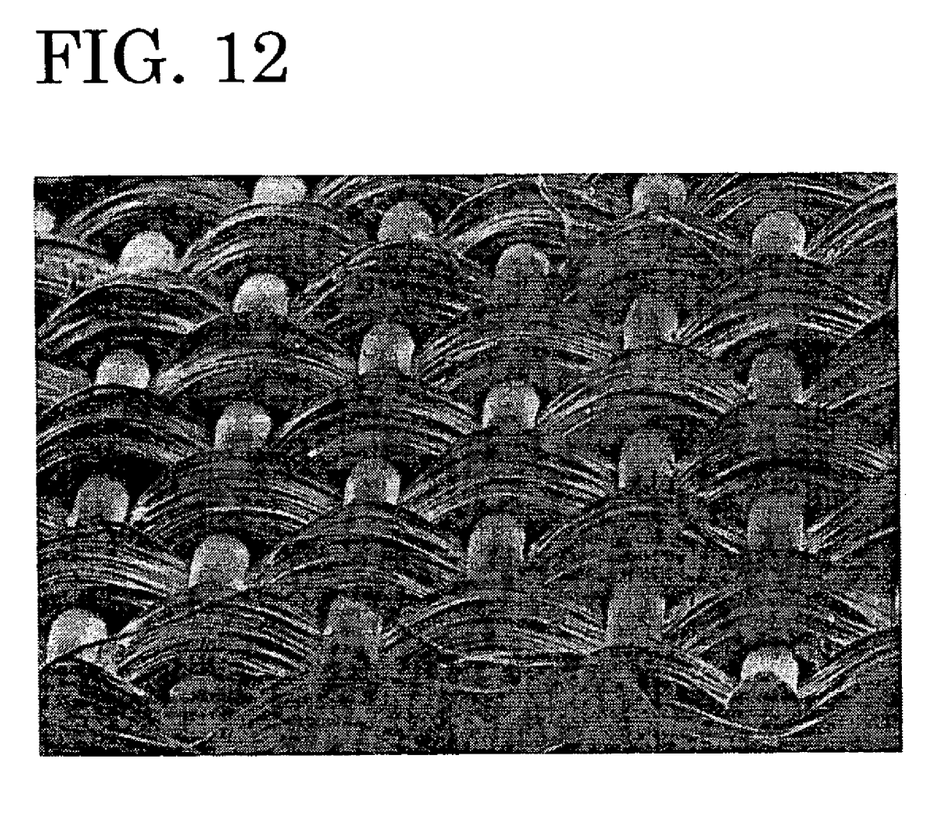
FIG. 12 is a photograph illustrating a magnified surface of the WTVP obtained in Comparative Example 2 for use in a SBVP.

The outer surfaces of the WTVPs obtained in Examples 1 and 3 and Comparative Example 2 for use in SBVPs were photographed as magnified. The photographs thus obtained are shown respectively in FIGS. 10 through 12. In FIGS. 10 and 11, no gap was observed in the interlaced parts of warps and wefts. In FIG. 12, gaps were observed between warps using monofilaments and wefts using multifilaments.

The results of the evaluation performed on the WTVPs which were produced in Examples 1–8 and Comparative Examples 1–7 are shown in Table 1.

TABLE 1

| | Construction | | | | Item of evaluation | | | |
|---|---|---|---|---|---|---|---|---|
| | Warps | | Wefts | | | | | |
| | (1) | (2) | (3) | (4) | (5) | (6) | (7) | (8) |
| Example 1 | 36/2 (18) | 0 | 94/170 (0.55) | 200 | 0.045 | 4 | 170 | 120 |
| Example 2 | 67/2 (33.5) | 0 | " | " | 0.066 | 4 | 70 | 130 |
| Example 3 | 67/4 (16.8) | 0 | " | " | 0.042 | 5.5 | 120 | 120 |
| Example 4 | 33/1 (33) 36/2 (18) Com. Fila. yarn. Total size 69 | 0 | " | " | 0.094 | 4 | 150 | 130 |
| Example 5 | 36/2 (18) 33/12 (2.8) Used at 50: 50 | 0 300 | " | " | 0.029 | 4 | 50 | 120 |
| Example 6 | 200/4 (50) | 0 | " | " | 0.118 | 4 | 70 | 150 |
| Example 7 | 90/5 (18) | 0 | " | " | 0.050 | 5.5 | 250 | 120 |
| Example 8 | 90/5 (18) | 100 | " | " | 0.050 | 7 | 400 | 140 |
| Com. Ex. 1 | 18/1 (18) | — | 94/170 (0.55) | 200 | 0.045 | 4 | 700 | 120 |
| Com. Ex. 2 | 33/1 (33) | — | " | " | 0.064 | 4 | 800 | 140 |
| Com. Ex. 3 | 108/6 (18) | 0 | " | " | 0.049 | 10 | 600 | 150 |
| Com. Ex. 4 | 56/24 (2.3) | 300 | " | " | 0.010 | 40 | 50 | 130 |
| Com. Ex. 5 | 222/48 (4.6) | 300 | " | " | 0.018 | 40 | 50 | 200 |
| Com. Ex. 6 | 90/5 (18) | 150 | " | " | 0.050 | 10 | 800 | 160 |
| Com. Ex. 7 | 125/216 (0.58) | — | 84/144 (0.58) | — | 0.010 | 40 | 50 | 120 |

In Table 1;
(1): Total size/Number of the single filament (Single filament size)
(2): Twist multiplier (times/meter)
(3): Total size/Number of the single filament (Single filament size)
(4): Twist multiplier (times/meter)
(5): Column strength (N/mm diameter)
(6): Radius of kink (mm)
(7): Coefficient of water permeability (mL/min/cm$^2$)
(8): Wall thickness (μm)
Com. Ex.: Comparative Example
Com. Fila.: Combined filament.

In Comparative Examples 1 and 2 on Table 1, the WTVPs which used monofilaments as the warps were favorable because they had large magnitudes of column strength of 0.045 and 0.064 N/mm of diameter within a specified range of 0.020–0.130 N/mm of diameter but were not favorable because they had large coefficients of water permeability of 700 and 800 mL/min/cm$^2$. Then, in Comparative Examples 4, 5, and 7 the WTVPs which used the conventional multifilaments formed of large numbers of single filaments and of small sizes of single filaments as the warps were favorable in respect that they had a small coefficient of water permeability of 50 mL/min/cm$^2$ but were not favorable in respect that they had small magnitudes of column strength of 0.010, 0.018, and 0.010 N/mm of diameter. Further, in both WTVPs of Comparative Example 3 in which a multifilament with a number of the single filament of 6, which was beyond the specified range of 2–5 sizes, was used as the warps and Comparative Example 6 in which a multifilament with the twist multiplier of 150 times/meter, which was beyond the specified range of 0–100 times/meter, the values of column strength were preferred to be 0.049 and 0.050 N/mm of diameter respectively, which were within the specified range of 0.020–0.130 N/mm of diameter, and the coefficients of water permeability were not preferred to be 600 and 800 mL/min/cm$^2$ respectively, since the single filaments did not form single lines.

Example 9

SBVPs were formed by causing wire rings disclosed in U.S. Pat. No. 5,976,179 to be sewn with intervals of 15 mm to WTVPs formed in a total length of 60 mm in Examples 1–8. These SBVPs were each implanted via a catheter into a resinous tube simulating a blood vessel and measuring 24 mm in inside diameter and 28 mm in outside diameter. The position for implanting the SBVP on the inside surface of the resinous tube was curved along the outer periphery of a cylinder 50 mm in radius and a branch was formed on the major curvature side of the position for implanting the SBVP with a tube 10 mm in inside diameter. When the water assumed to be blood was made to flow into the resinous tube, the tube held the inner cavity thereof intact without suffering the shape thereof crushed by the flow of water and leaked no water through the branch. Thus, it could acquire a satisfactory result of implant.

Comparative Example 8

SBVPs were formed by repeating the procedure of Example 9, except that the WTVPs in Comparative Examples 1–7 were used. These SBVPs were each implanted in the same resinous tube as used in Example 9 and the water assumed to be blood was made to flow into the resinous tube.

As a result, the SBVPs of Comparative Examples 1, 2, 3, and 6 induced conspicuous leak of water through the branches because of large coefficients of water permeability, though they did not suffer their shapes to be crushed by the flow of water. Thus, they were suspected to be incapable of satisfactorily blocking the flow of blood into an aneurysm in the case of clinical use.

In the SBVPs of Comparative Examples 4 and 7, because of small magnitudes of column strength, the ring at the most proximal portion could not be easily disposed in a stable manner perpendicularly to the respective tube during the course of implant of the prostheses in the tubes. The SBVPs also showed a sign of partial decrease of the cross section of the inner cavity due to the occurrence of a kink. Further, the ring at the most proximal portion showed an inclination of being moved slightly toward the peripheral side by the flow of water. Thus, the SBVPs were suspected to have the possibility of starting from the position of implant or inducing blockage of the inner cavity after a protracted implant.

In Comparative Example 5, on account of a large wall thickness, the SBVP during passage through a catheter offered an increased sliding resistance inside the catheter and rendered the operation of implant difficult.

The entire disclosure of Japanese Patent Application No. 2002-078626 filed on Mar. 20, 2002 including specification, claims, drawings, and summary are incorporated herein by reference in its entirety.

What is claimed is:

1. A woven tubing for use in a stent blood vascular prosthesis, comprising:
   a multifilament warp element formed of only two to five single filaments; and
   a weft element;
   wherein the warp element and weft element are woven in such a manner that all of the single filaments forming the multifilament warp element are disposed in a single line.

2. A woven tubing according to claim 1, wherein a size of the single filament is in the range of 5.5–50 dtex.

3. A woven tubing according to claim 1, wherein a total size of the multifilament warp element is in the range of 11 to 250 dtex.

4. A woven tubing according to claim 1, wherein the weft element includes a multifilament having a single filament size in the range of 0.1–3.5 dtex and formed of 10–1,000 single filaments.

5. A woven tubing according to claim 1, wherein the warp element and weft element are made of a polyester fiber, respectively.

6. A woven tubing according to claim 5, wherein the polyester fiber is at least one member selected from the group consisting of polyethylene terephthalate, polybutylene terephthalate, polyester-polyether block copolymers, and composite fibers thereof.

7. A woven tubing according to claim 1, wherein the tubing is a crimped tubing.

8. A woven tubing according to claim 1, wherein the tubing has a branched part.

9. A stent blood vascular prosthesis, comprising:
   a woven tubing recited in claim 1; and
   a stent to which the woven tubing is attached.

10. A woven tubing for use in a stent blood vascular prosthesis, comprising:
    a plurality of woven warp elements and weft elements;
    at least apart-of one of the warp elements being a multifilament warp element formed of at least two single filaments and not more than five single filaments; and
    the warp elements and the weft elements being woven in such a manner that all of the single filaments of the at least one multifilament warp element are disposed in a single line between the weft elements.

11. A woven tubing according to claim 10, wherein a size of the single filament is in the range of 5.5–50 dtex.

12. A woven tubing according to claim 10, wherein a total size of the at least one multifilament warp element is in the range of 11 to 250 dtex.

13. A woven tubing according to claim 10, wherein at least one of the weft elements includes a multifilament having a single filament size in the range of 0.1–3.5 dtex and formed of 10–1,000 single filaments.

14. A woven tubing according to claim 10, wherein the warp elements and weft elements are made of a polyester fiber, respectively.

15. A woven tubing according to claim 14, wherein the polyester fiber is at least one member selected from the group consisting of polyethylene terephthalate, polybutylene terephthalate, polyester-polyether block copolymers, and composite fibers thereof.

16. A woven tubing according to claim 10, wherein the tubing is a crimped tubing.

17. A woven tubing according to claim 10, wherein the tubing has a branched part.

18. A stent blood vascular prosthesis, comprising:
    a woven tubing recited in claim 10; and
    a stent to which the woven tubing is attached.

19. A woven tubing according to claim 10, wherein the woven tubing includes a total number of warps, the total number of warps being comprised of a plurality of the multifilament warp elements, and a ratio of the multifilament warp elements to other threads forming the tubing being in a range of 25:75–100:0, assuming the total number of warps forming the tubing is 100.

* * * * *